US009586090B2

(12) United States Patent
Watterson et al.

(10) Patent No.: US 9,586,090 B2
(45) Date of Patent: Mar. 7, 2017

(54) SYSTEM AND METHOD FOR SIMULATING REAL WORLD EXERCISE SESSIONS

(71) Applicant: ICON Health & Fitness, Inc., Logan, UT (US)

(72) Inventors: Scott R. Watterson, Logan, UT (US); Mark D. Watterson, Logan, UT (US); David Watterson, Logan, UT (US)

(73) Assignee: ICON Health & Fitness, Inc., Logan, UT (US)

( * ) Notice: Subject to any disclaimer, the term of this patent is extended or adjusted under 35 U.S.C. 154(b) by 101 days.

(21) Appl. No.: 13/860,310

(22) Filed: Apr. 10, 2013

(65) Prior Publication Data

US 2013/0274069 A1 Oct. 17, 2013

Related U.S. Application Data

(60) Provisional application No. 61/623,441, filed on Apr. 12, 2012.

(51) Int. Cl.
*A63B 71/00* (2006.01)
*A63B 24/00* (2006.01)
(Continued)

(52) U.S. Cl.
CPC ...... *A63B 24/0087* (2013.01); *A63B 22/0023* (2013.01); *A63B 22/0235* (2013.01); *A63B 24/0075* (2013.01); *A63B 21/0051* (2013.01); *A63B 21/012* (2013.01); *A63B 22/0056* (2013.01); *A63B 22/0605* (2013.01); *A63B 2022/0682* (2013.01); *A63B 2024/009* (2013.01); *A63B 2024/0093* (2013.01); *A63B 2071/068* (2013.01); *A63B 2071/0625* (2013.01); *A63B 2071/0638* (2013.01);
(Continued)

(58) Field of Classification Search
CPC ............ A63B 22/0023; A63B 24/0075; A63B 24/0087; A63B 2024/009; A63B 2071/0625; A63B 2071/0638; A63B 2071/0641; A63B 2071/0644
USPC .............................................. 482/1–9, 51–65
See application file for complete search history.

(56) References Cited

U.S. PATENT DOCUMENTS 5,137,501 A * 8/1992 Mertesdorf ..................... 482/57
5,888,172 A * 3/1999 Andrus ................ A61B 5/6887
434/247

(Continued)

*Primary Examiner* — Loan H Thanh
*Assistant Examiner* — Gregory Winter
(74) *Attorney, Agent, or Firm* — Maschoff Brennan

(57) ABSTRACT

In an exercise system having a remote communication system adapted to communicate with an exercise device, a method for generating an exercise program includes receiving route information identifying a route traveled by an individual during a real world exercise session, receiving audio information identifying a musical selection listened to by the individual during the real world exercise session, using the route information and the audio information to generate an exercise program. The exercise program includes control signals that cause an exercise device to substantially simulate the topographical characteristics of the route traveled by the individual during the real world exercise session, and audio signals representative of the musical selection listened to by the individual during the real world exercise session so that the musical selection is presented during a performance of the exercise program.

21 Claims, 9 Drawing Sheets

(51) Int. Cl.
*A63B 22/00* (2006.01)
*A63B 22/02* (2006.01)
*A63B 21/005* (2006.01)
*A63B 21/012* (2006.01)
*A63B 22/06* (2006.01)
*G06F 19/00* (2011.01)
*A63B 71/06* (2006.01)

(52) U.S. Cl.
CPC ... *A63B 2071/0691* (2013.01); *A63B 2220/12* (2013.01); *A63B 2220/70* (2013.01); *A63B 2225/20* (2013.01); *A63B 2225/50* (2013.01); *G06F 19/3481* (2013.01)

(56) References Cited

U.S. PATENT DOCUMENTS

| | | | |
|---|---|---|---|
| 6,152,856 A * | 11/2000 | Studor et al. | 482/8 |
| 6,336,891 B1 * | 1/2002 | Fedrigon et al. | 482/8 |
| 6,450,922 B1 * | 9/2002 | Henderson et al. | 482/8 |
| 7,217,224 B2 * | 5/2007 | Thomas | 482/8 |
| 7,625,315 B2 * | 12/2009 | Hickman | A63B 24/0062 482/1 |
| 8,029,415 B2 | 10/2011 | Ashby et al. | |
| 8,101,843 B2 * | 1/2012 | Turner | 84/612 |
| 8,103,517 B2 * | 1/2012 | Hinnebusch | A63B 24/0084 482/4 |
| 8,200,323 B2 * | 6/2012 | DiBenedetto et al. | 600/519 |
| 8,568,278 B2 * | 10/2013 | Riley et al. | 482/9 |
| 8,704,068 B2 * | 4/2014 | Bowen | 84/612 |
| 8,777,815 B2 * | 7/2014 | Case et al. | 482/8 |
| 8,814,754 B2 * | 8/2014 | Weast et al. | 482/8 |
| 8,951,168 B2 * | 2/2015 | Baudhuin | 482/57 |
| 2003/0139254 A1 * | 7/2003 | Chang | 482/1 |
| 2008/0234113 A1 * | 9/2008 | Einav | 482/66 |
| 2009/0209393 A1 * | 8/2009 | Crater et al. | 482/9 |
| 2009/0270227 A1 * | 10/2009 | Ashby et al. | 482/8 |
| 2010/0056340 A1 * | 3/2010 | Ellis et al. | 482/4 |
| 2010/0216601 A1 * | 8/2010 | Saalasti et al. | 482/8 |
| 2010/0222179 A1 * | 9/2010 | Temple et al. | 482/8 |
| 2012/0015779 A1 * | 1/2012 | Powch et al. | 482/9 |
| 2012/0077641 A1 * | 3/2012 | Dyer | A63B 22/00 482/8 |
| 2013/0210580 A1 * | 8/2013 | Watterson et al. | 482/8 |

* cited by examiner

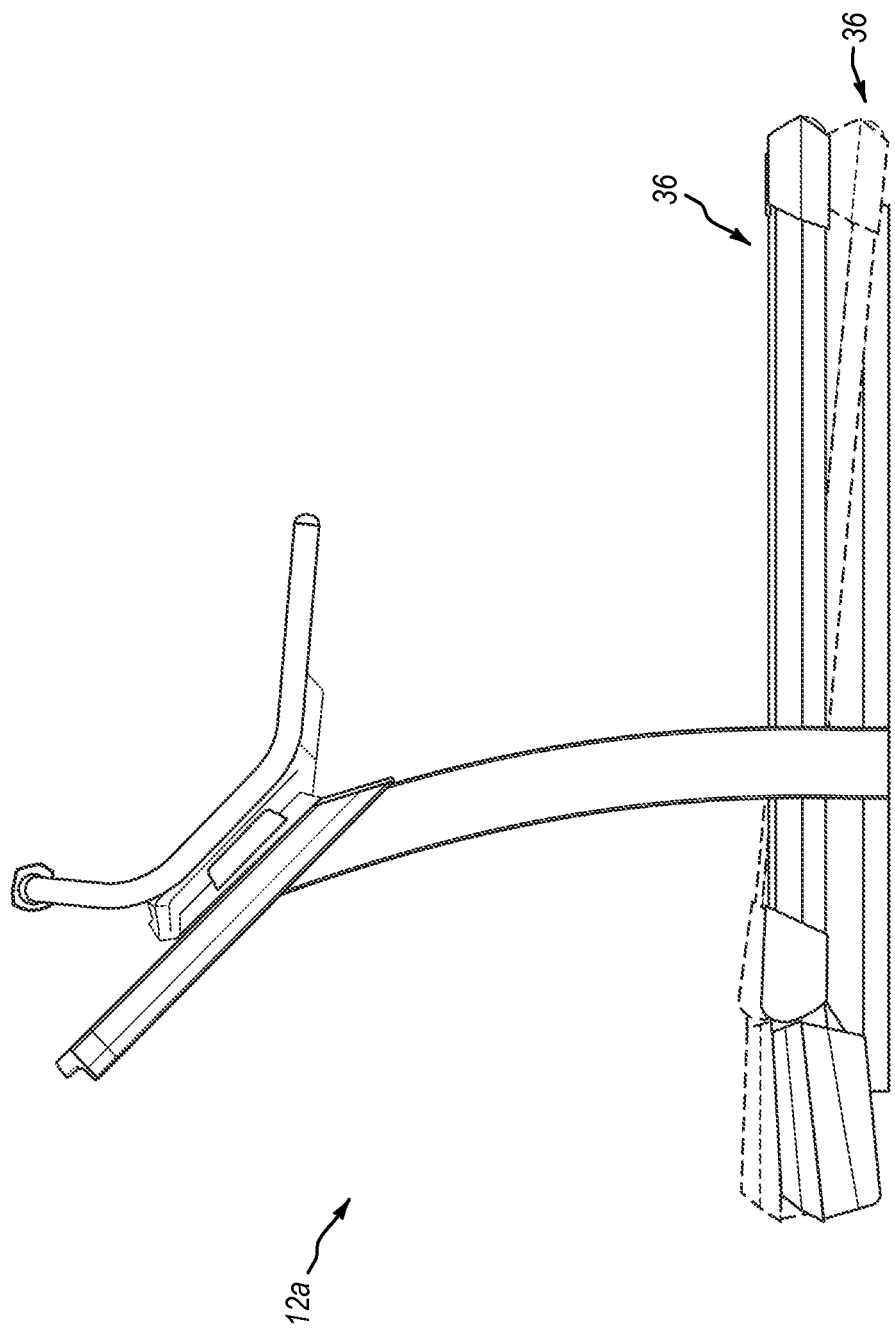

SYSTEM AND METHOD FOR SIMULATING REAL WORLD EXERCISE SESSIONS

CROSS-REFERENCE TO RELATED APPLICATIONS

This application claims priority to U.S. Provisional Patent Application No. 61/623,441 filed Apr. 12, 2012.

TECHNICAL FIELD

The present invention relates to exercise related systems and methods. More specifically, the invention relates to systems and methods for simulating a real world exercise session on an exercise device.

BACKGROUND

In an attempt to improve their health and physical conditioning, consumers are purchasing exercise devices in record quantities. One common challenge with exercise equipment is motivating the purchaser to use the device on a consistent and ongoing basis. This lack of motivation can be a result of the repetitive nature of the exercises and exercise routines that a user can perform on a specific exercise device as well as the versatility of the exercise devices.

In an effort to maintain the motivation necessary for the user of an exercise device to consistently use the exercise device, some exercise devices simulate the outdoors by creating exercise programs that reflect the terrain of real world locations. For example, U.S. Pat. No. 8,029,415 discloses a system where an individual may identify a street, road, or path that the individual wants to traverse during the exercise session. An exercise program is created that simulates the terrain of the chosen exercise route. For example, an exercise program created for a treadmill may include control signals that increase and decrease tread base inclination levels consistent with the terrain of the chosen exercise route. In addition, images of the chosen exercise route may be presented to the user on display screens.

SUMMARY

In one embodiment, a method for generating an exercise program in an exercise system having a remote communication system adapted to communicate with an exercise device includes receiving route information identifying a route traveled by an individual during a real world exercise session. The method also includes receiving audio information identifying a musical selection listened to by the individual during the real world exercise session. The method further includes using the route information and the audio information to generate an exercise program, where the exercise program includes control signals that cause an exercise device to substantially simulate the topographical characteristics of the route traveled by the individual during the real world exercise session and audio signals representative of the musical selection listened to by the individual during the real world exercise session, the musical selection being presented during a performance of the exercise program.

In another aspect that may be combined with any of the aspects herein, the route information is received from a device that is communicatively connected to the remote communication system, the device monitoring the route traveled by the individual.

In another aspect that may be combined with any of the aspects herein, the method further includes retrieving data from a third party regarding the route traveled by the individual during the real world exercise session in order to generate the control signals.

In another aspect that may be combined with any of the aspects herein, the method further includes retrieving data from a third party regarding the musical selection listened to by the individual during the real world exercise session in order to generate the audio signals.

In another aspect that may be combined with any of the aspects herein, the exercise program further comprises display signals that cause the exercise device to display images of the route traveled by the individual during the real world exercise session.

In another aspect that may be combined with any of the aspects herein, the method further includes retrieving data from a third party regarding the route traveled by the individual during the real world exercise session in order to generate the display signals.

In another aspect that may be combined with any of the aspects herein, the display signals comprise video images.

In another aspect that may be combined with any of the aspects herein, the method further includes synchronizing the control signals and the display signals.

In another aspect that may be combined with any of the aspects herein, the control signals cause an actuator associated with a treadmill tread base to adjust an inclination of the tread base.

In another aspect that may be combined with any of the aspects herein, the control signals also cause an actuator associated with a treadmill tread base to adjust a side to side tilt of the tread base.

In another aspect that may be combined with any of the aspects herein, the control signals cause an actuator associated with pedals of an exercise device to adjust a rotational resistance applied to the pedals.

In another aspect that may be combined with any of the aspects herein, the control signals cause an actuator associated with an exercise device frame to adjust a tilt of the device frame.

In another aspect that may be combined with any of the aspects herein, the method further includes making the exercise program available for download to an exercise device.

In another aspect that may be combined with any of the aspects herein, the exercise program is made available for download to the exercise device via the internet.

In another aspect that may be combined with any of the aspects herein, the audio information identifying a musical selection comprises a playlist of songs.

In another aspect that may be combined with any of the aspects herein, an exercise system may include an exercise device having an audio output device and a movable element that moves during the performance of an exercise.

In another aspect that may be combined with any of the aspects herein, the movable element may include at least one selectively adjustable operating parameter.

In another aspect that may be combined with any of the aspects herein, the exercise system may include a remote communication system that is in communication with the exercise device. The remote communication system may be receptive to information identifying a real world exercise route traveled by an individual during an exercise session and receptive to auditory information identifying a playlist of songs that the individual listened to during the exercise session.

In another aspect that may be combined with any of the aspects herein, the remote communication system retrieves data relating to the real world exercise route and data relating to the playlist of songs that the individual listened to during the exercise session.

In another aspect that may be combined with any of the aspects herein, the remote communication system uses the retrieved data to create an exercise program that includes control signals that selectively adjust the at least one selectively adjustable operating parameter of the movable element to simulate terrain characteristics of the real world exercise route, display signals that include visual images of the real world exercise route, and audio signals representative of the playlist of songs listened to by the individual during the exercise session.

In another aspect that may be combined with any of the aspects herein, the audio output device is a speaker.

In another aspect that may be combined with any of the aspects herein, the remote communication system communicates with the exercise device via a portable memory device.

In another aspect that may be combined with any of the aspects herein, the control signals selectively adjust an inclination level of a treadmill tread base.

In another aspect that may be combined with any of the aspects herein, a computer system includes one or more processors, system memory, and one or more computer storage media having stored thereon computer-executable instructions which, when executed by the one or more processors, cause the computer system to implement a method for presenting analytical data.

DESCRIPTION OF THE DRAWINGS

FIG. 2 is a side illustration of a the treadmill shown in FIG. 1 with the tread base shown in a neutral position, and an inclined position featured in phantom view.

DETAILED DESCRIPTION

Figure 1:
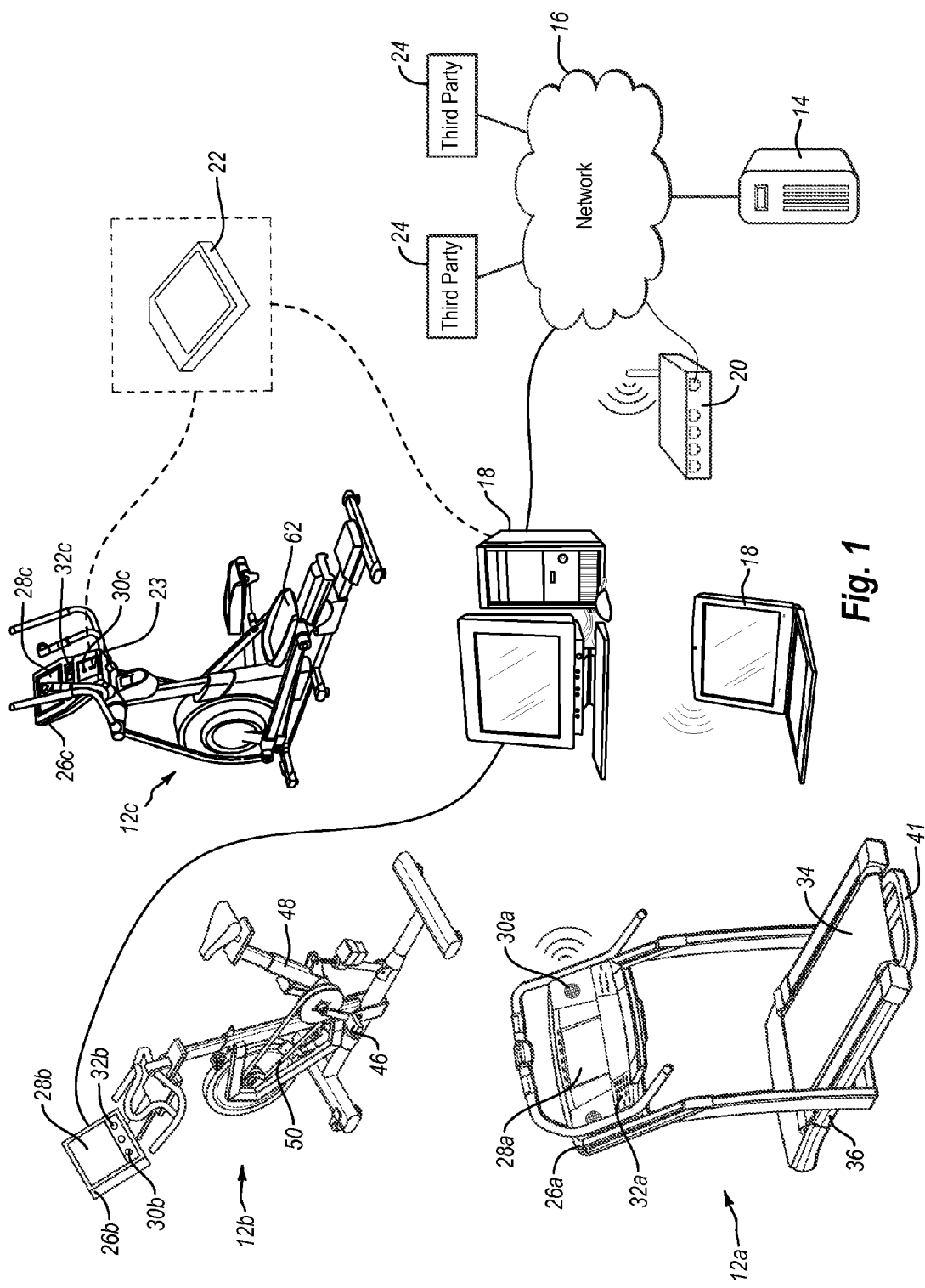
FIG. 1 illustrates an exercise system according to one embodiment of the present invention.

Exercise system 10, illustrated in FIG. 1, includes exercise devices 12, such as a treadmill 12a, an exercise cycle 12b, and an elliptical machine 12c. Each of exercise devices 12 are in communication with and may receive exercise programming from a communication system 14 (e.g., a website). Communication system 14 may comprise one or more computers and/or computer systems. The communication between communication system 14 and exercise devices 12 may be accomplished via a direct connection between communication system 14 and exercise devices 12 or an indirect connection between communication system 14 and exercise devices 12. For example, exercise devices 12 may communicate with communication system 14 via a network 16. In addition, exercise devices 12 may communicate with communication system 14 via personal computers 18, wireless router 20, and/or a portable data storage device, such as memory card 22.

Specifically, the exercise programming may be initially downloaded to personal computers 18, which may then communicate the exercise programming to one or more of exercise devices 12. The communication of the exercise programming from personal computers 18 to one or more of exercise devices 12 may be through a wired or wireless connection. Alternatively, the exercise programming may be communicated via memory card 22. For example, memory card 22 may receive an exercise program from personal computers 18 and transmit this programming to one or more of exercise devices 12. In still other embodiments, rather than downloading the exercise programming with personal computers 18 and then storing it on memory card 22, the exercise programming may be stored on memory card 22 directly by communication system 14. Memory card 22 may then be made available to a user of exercise devices 12. Further still, the exercise programming may be delivered to exercise devices 12 over network 16 via wireless router 20. Exercise programming may be streamed from communication system 14 to exercise devices 12 or downloaded and stored by exercise devices 12.

The exercise programming received from communication system 14 may simulate actual real world exercise sessions performed by one or more individuals. For example, an individual may provide communication system 14 with information regarding a real world exercise session that he or she previously performed. This information provided to communication system 14 may include the route, trail, or path that the individual traveled as well as an audio selection that the individual listened to during the exercise session or selected. This information may be submitted to communication system 14 via input devices, such as buttons on exercise devices 12, personal computers 18, and/or another computing device that are in communication with communication system 14. For example, a GPS watch, telephone, or another portable device may automatically upload information regarding an individual's real world exercise session.

Based upon the information submitted by the individual, communication system 14 may create an exercise program that includes control signals, display signals, and/or audio signals that simulate the individual's real world exercise session. For example, the control signals may simulate the terrain that the individual encountered during the real world exercise session. The display signals may illustrate images of the terrain and scenery that the individual encountered during the real world exercise session. The audio signals may simulate the sounds that the individual heard during the real world exercise session. These sounds may include sounds of nature or other sounds such as music, as would be the case if the individual was listening to a portable music device during the performance of the exercise session. The audio signals may also include other audio selections chosen by the individual, such as the individual's exercise song playlist. In one embodiment, an exercise session comprises control signals that simulate the terrain that the individual encountered during a real world exercise session and audio signals that include a musical selection listened to by the individual during the exercise session.

In order to create the exercise program, communication system 14 may communicate with and gather data from one or more third parties 24. As described in more detail hereafter, these third parties may provide communication system 14 with terrain data, image data, and/or audio data. Once created, an exercise program may be delivered to and executed by exercise devices 12.

As illustrated in FIG. 1, exercise devices 12 each include control consoles 26a, 26b, and 26c. Each of exercise devices 12 also include one or more output devices, which are configured to present information to a user. For example, control consoles 26a-26c include display screens 28a, 28b, and 28c, respectively. A display screen, according to the present invention, may include video displays, liquid crystal displays (LCD), light emitting diodes (LEDs), cathode ray tube (CRT) displays, electroluminescent displays (ELD), gas-plasma displays, thin film transistor (TFT) displays, virtual reality (VR) displays, and the like.

Each of exercise devices 12 also includes one or more audio output devices 30a, 30b, and 30c. An audio output device can be any device that presents or makes available audio signals. For example, an audio output device may comprise a speaker, a wired audio out port (such as an RCA-type audio port), a wireless audio port, or the like. A wireless audio port may use Bluetooth or another wireless technology to present audio signals. For example, audio output device 30a on treadmill 12a comprises a speaker. Audio output device 30b on exercise cycle 12b comprises a wired audio out port that may be connected to one or more external speakers, such as headphones. Audio output device 30c on elliptical machine 12c comprises a Bluetooth wireless audio out port that may be connected to one or more wireless external speakers, such as Bluetooth enabled headphones.

Each of exercise devices 12 further includes one or more input devices 32a, 32b, and 32c. Input devices enable a user to input information, controls and/or other commands. For example, using one or more input devices, a user may vary one or more operating parameters of exercise devices 12, such as time, distance, speed, incline, tilt, etc. Input devices may also include a start button, and/or a stop or pause button. It may be appreciated that each of the above-recited input devices may be buttons, switches, rheostats, potentiometers, touch sensitive controls, voice activated controllers, and the like.

Input devices 32 may also enable a user to access communication system 14 and/or obtain maps, topographical information, pictures or videos of real world places, or other information via network 16, whether such information is from communication system 14, one or more third parties 24, or from one of a variety of other hardware and/or software modules that are accessible via network 16. For example, an input device may allow a user to access the Internet to find maps, topographical data, pictures, and/or videos of real world locations, routes, paths, courses, and the like. Input devices 32 may also enable an individual to provide information regarding a real world exercise session to communication system 14. For example, an individual may use input devices 32 to identify the route he or she traveled, whether the individual performed the exercise session on foot or rode a bike, the temperature and other weather conditions during the exercise session, the audio selection that the individual listened to during the exercise session, and the like.

One or more input devices may also function as a selector of connectivity of treadmill 21a, exercise cycle 12b, and or elliptical machine 12c to communication system 14, and optionally one or more third parties 24, whether such connectivity is direct from treadmill 12a, exercise cycle 12b, or elliptical machine 12c or via computer 18 or wireless router 17. In addition, an indicator light (not shown) may demonstrate when a connection has been established between exercise devices 12 and communication system 14.

As discussed above, the connection achieved between exercise devices 12 and communication system 14 may be made in a variety of ways. For example, treadmill 12a includes a wireless port that allows wireless communication with communication system 14, either directly or through network 16, via personal computers 18 and/or wireless router 20. Exercise cycle 12b includes a wired port that allows a wired communication with communication system 14 either directly or through network 16 via personal computers 18. Elliptical machine 12c may communicate with communication system 14 via a memory card 22. Specifically, elliptical machine 12c includes a portable storage device port 23 to which memory card 22 may be inserted. Devices, such as personal computers 18, may also include a portable storage device port into which memory card 22 may be inserted. Data, files, exercise programming, and media may be communicated from communication system 14 to personal computers 18, which may store the data, files, exercising programming, and media on memory card 22. Memory card 22 may then be removed from computer 18 and inserted into portable storage device port 23 on elliptical machine 12c so that the data, files, exercising programming, and media can be provided to elliptical machine 12c.

Referring back to FIG. 1, exercise devices 12 further include one or more moveable members. A moveable member can be any part of an exercise device that moves during a user's performance of an exercise on an exercise device. The movement of a moveable member may be selectively adjusted by an actuator. An actuator may be any mechanism that selectively adjusts the movement of a moveable member and may include a motor, brake, or other mechanism.

For example, the moveable members on treadmill 12a include a belt 34 and tread base 36. An actuator (e.g., a belt motor) may selectively adjust the speed at which belt 34 rotates. In addition to the ability to control and vary the speed of belt 34, treadmill 12a also permits the degree of incline of tread base 36 relative to the floor, or other surface upon which tread base 36 rests, to be varied. As depicted in solid lines in FIG. 2, tread base 36 can be oriented in a neutral or level position. In the neutral or level position, tread base 36 is substantially horizontal. Additionally, as illustrated in phantom lines in FIG. 2, tread base 36 can be oriented in an inclined position such that the front portion of tread base 36 is above the neutral position. Tread base 36 can also be oriented in a declined position in which the front portion of tread base 36 drops below the neutral position.

Figure 4:
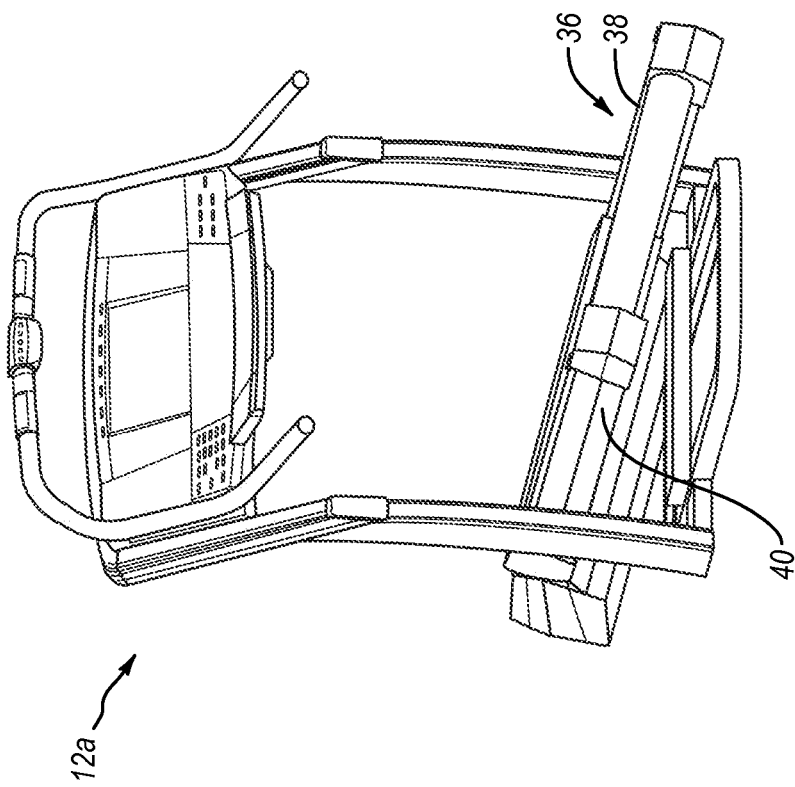
FIG. 4 is another rear perspective illustration of the treadmill shown in FIG. 1 with the tread base in a second tilted position.
Figure 3:
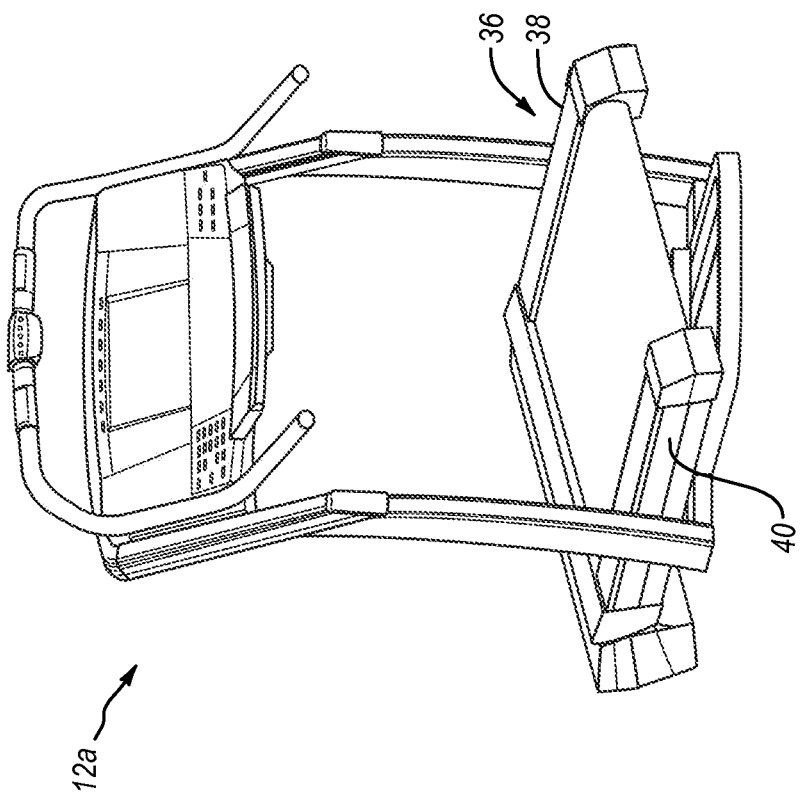
FIG. 3 is a rear perspective illustration of the treadmill shown in FIG. 1 with the tread base in a first tilted position.

Treadmill 12a also permits tread base 36 to be tilted from side to side. As depicted in FIGS. 3 and 4, tread base 36 can be tilted such that one side of tread base 36 is higher than the other. For instance, FIG. 3 illustrates tread base 36 tilted so that one side of tread base 36, specifically side rail 38 is higher than the other side of tread base 36, specifically side rail 40. FIG. 4 illustrates the opposite configuration of tread base 36 where tread base 36 is tilted so that side rail 40 is higher than side rail 38.

Figure 5:
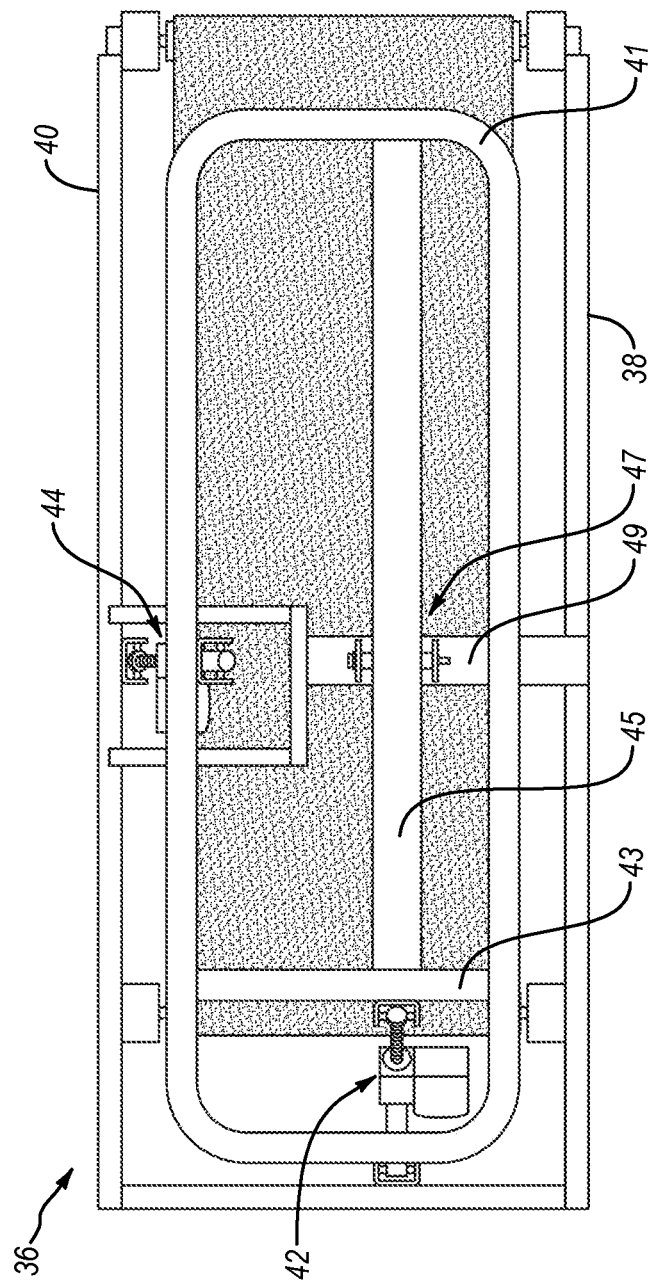
FIG. 5 is a bottom view of the treadmill illustrated in FIGS. 1 through 4 showing some of the incline/decline and tilting mechanisms of the treadmill.

FIG. 5 illustrates a bottom view of treadmill 12a. The inclination/declination of tread base 36 can be accomplished through the use of an actuator. Specifically, an incline mechanism 42 raises and lowers one end of tread base 36 relative to the other end. The side to side tilting of tread base 36 can be accomplished through the use of another actuator. Specifically, tilt mechanism 44, raises and lowers one side of tread base 36 relative to the other side. Incline mechanism 42 and tilt mechanism 44 are interconnected between tread base 36 and a base frame 41. Base frame 41 includes a cross bar member 43 and a support member 45.

A bracket 47 facilitates the inclination, declination, and tilting of tread base 36 relative to base frame 41. As best seen in FIG. 5, support member 45 is generally in line with incline mechanism 42. Tread base 36 also includes a cross member 49 that extends between side rails 38 and 40. Cross member 49 is generally in line with tilt mechanism 44. Cross member 49 extends across and over support member 45 such that support member 45 and cross member 49 are generally perpendicular to one another.

Bracket 47 pivotally couples together tread base 36 and base frame 41 such that tread base 26 is allowed to tilt relative to bracket 47 about an axis that is substantially parallel to a longitudinal axis of tread base 26. Bracket 47 is coupled to base frame 41 in a similar manner as tread base 26. Specifically, support member 45 is pivotally coupled to bracket 47. Coupling support member 45 to bracket 47 in this manner enables bracket 47 and tread base 36 to pivot relative to base frame 41 about an axis that is substantially perpendicular to a longitudinal axis of tread base 36. Pivoting of bracket 47 and tread base 36 in this manner allows tread base 36 to be inclined or declined as described herein.

Each of the actuators in treadmill 12a, including incline mechanism 42, tilt mechanism 44, and the belt motor, may be electrically connected to a treadmill controller. In response to various user inputs or other control signals, the treadmill controller may control the operation of incline mechanism 42, tilt mechanism 44, and the belt motor, thereby controlling the incline/tilt of tread base 36 and the speed of belt 34. A treadmill controller can be incorporated within any part of treadmill 12a, such as in tread base 36 or control console 26a. A treadmill controller can also be incorporated within personal computers 18.

The ability to change the inclination level and side to side tilt of tread base 36 allows treadmill 12a to more closely simulate outdoor terrain. Typical walks or runs outside, for example, often involve inclines, declines, flat surfaces, as well as surfaces that are not level from side to side. Each of these terrain types can be accommodated and replicated by tread base 36. Thus, treadmill 12a can more closely simulate typical outdoor terrain.

The moveable members on exercise cycle 12b include a pedal assembly 46 and frame structure 48. An actuator (e.g., braking mechanism 50) may selectively adjust the rotational resistance applied to pedal assembly 46. Braking mechanism 50 can comprise a friction brake, a magnetic brake, or any other suitable brake for controlling the rotational resistance applied to pedal assembly 46. In addition to the ability to control and vary the speed and resistance of pedal assembly 46, exercise cycle 12b also permits frame structure 48 to be positioned in a forwardly tilted and rearwardly tilted orientations.

Figure 6:
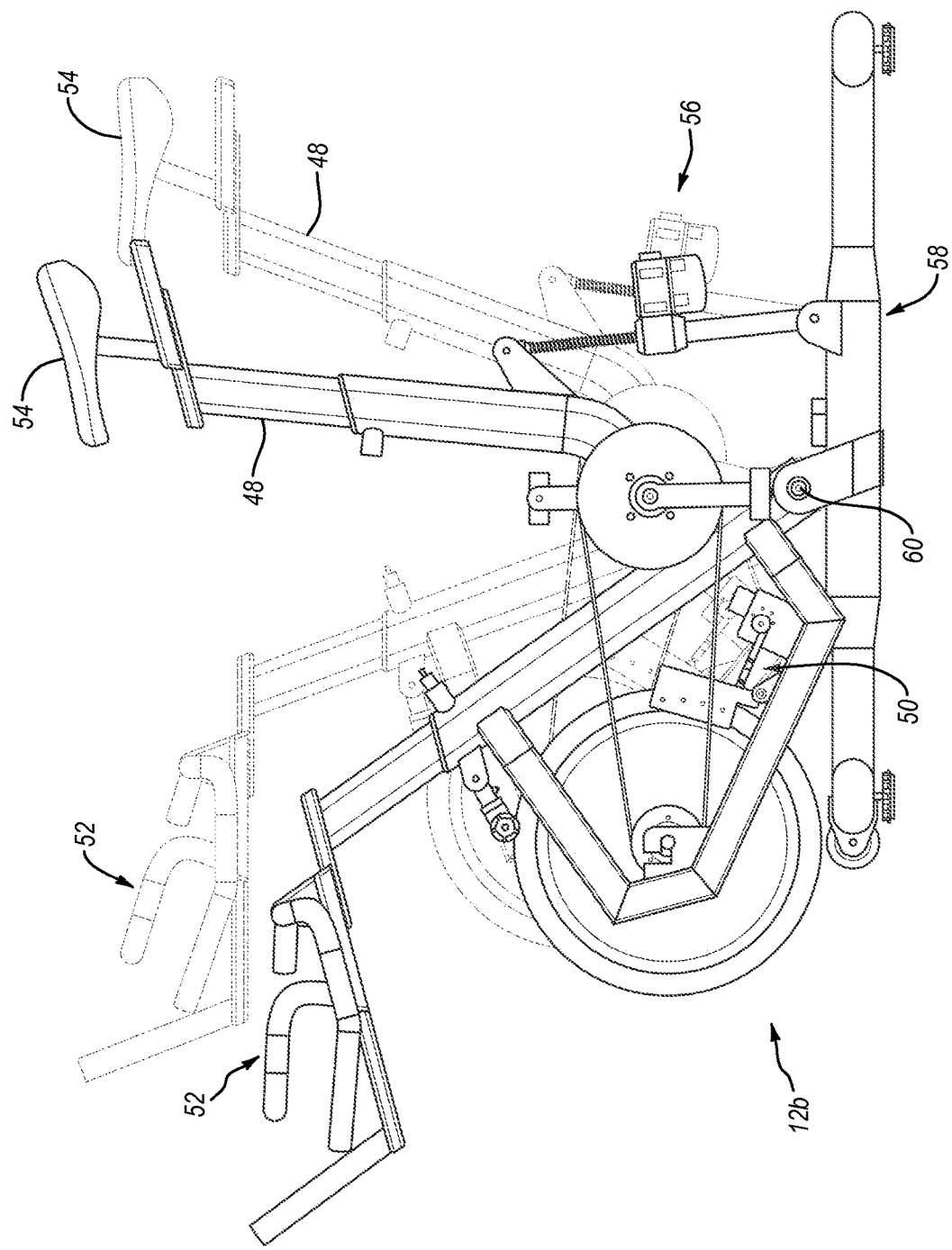
FIG. 6 is a side illustration of the exercise cycle shown in FIG. 1 with the upright frame shown in a forward tilted position, and a neutral position featured in phantom view.
Figure 7:
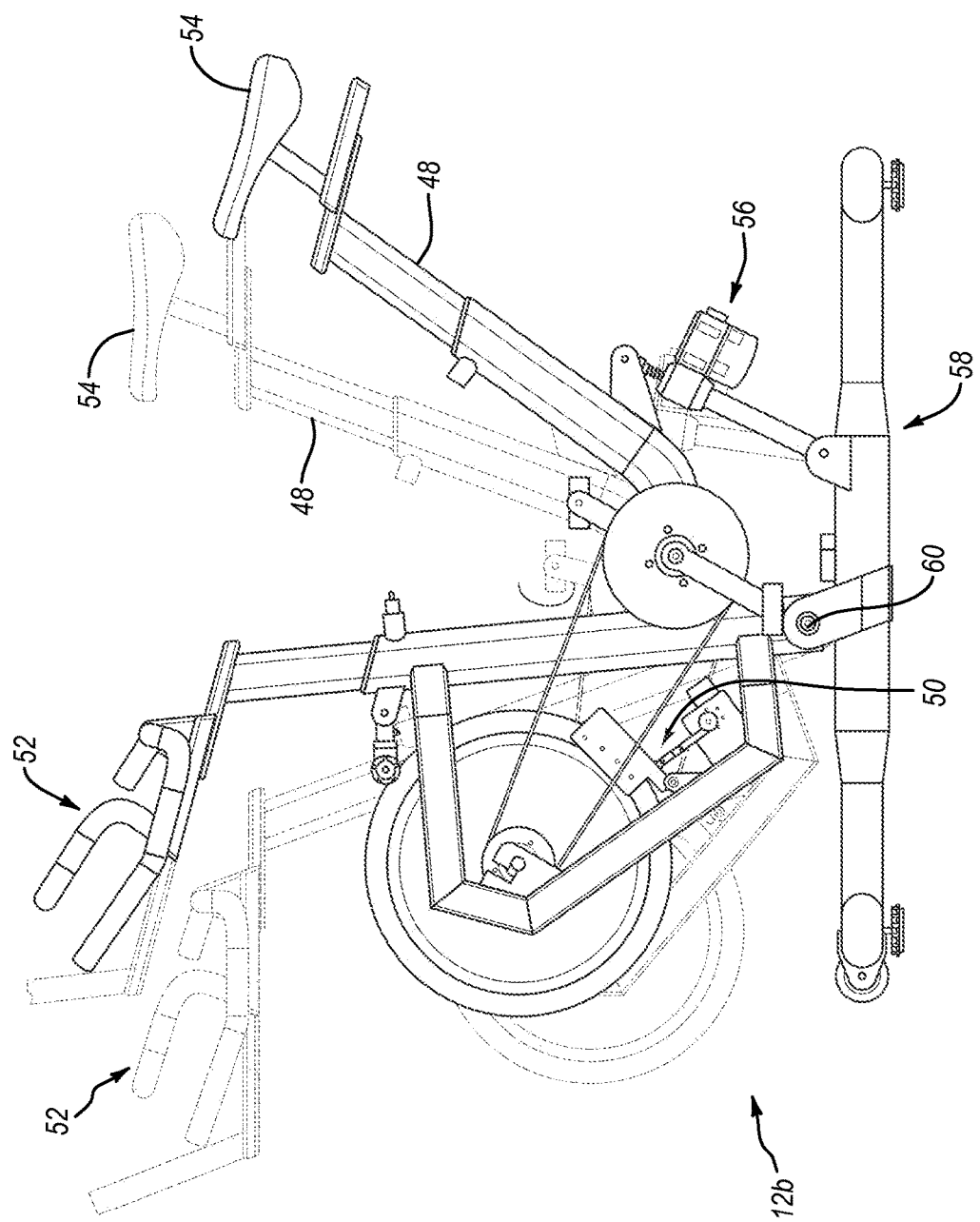
FIG. 7 is another side illustration of the exercise cycle shown in FIG. 1 with the upright frame shown in a backward tilted position, and a neutral position featured in phantom view.

As depicted in FIG. 6 in phantom lines, frame structure 48 can be oriented in a neutral position. In the neutral position, handle bar assembly 52 and seat 54 are at generally the same vertical height. When frame structure 48 is in the neutral position, a user sitting on seat 54 will feel that he or she is sitting on a bicycle that is on a level surface. Additionally, as illustrated in solid lines in FIG. 6, frame structure 48 can be oriented in a forwardly tilted position such that the handle bar assembly 52 is vertically below the neutral position and seat 54. Tilting frame structure 48 forward as illustrated in FIG. 6 enables a user to simulate riding down a hill. As depicted in FIG. 7, frame structure 48 can also be oriented in a rearwardly tilted position in which the handle bar assembly 52 is vertically above the neutral position and seat 54. Typical bicycle rides outside, for example, involve inclines and declines as well as flat surfaces, each of which can be accommodated and replicated by the tilting ability of frame structure 48. Thus, exercise cycle 12b is able to more closely simulate a typical outdoor bicycle ride.

The forward and rearward tilting of frame structure 48 can be accomplished via a pivot and an actuator (e.g., extension mechanism 56). Frame structure 48 is pivotally coupling to a support base 58 by a pivot 60 as depicted in FIGS. 6 and 7. Pivot 60 allows frame structure 48 to tilt forward and backward as described above. Pivot 60 can include a pin that extends through a portion of support base 58 and through frame structure 48. Pivot 60 can also include one or more stops to limit the tilting of frame structure 48 within a desired range.

While pivot 60 allows frame structure 48 to tilt forward and backward, extension mechanism 56 controls the tilting of frame structure 48. In the illustrated embodiment, extension mechanism 56 is coupled between support base 58 and frame structure 48. Extension mechanism 56 raises or lowers frame structure 48 relative to support base 58, thereby determining the tilt of frame structure 48.

Each of the actuators in exercise cycle 12b, including braking mechanism 50 and extension mechanism 56, may be electrically connected to an exercise cycle controller. The exercise cycle controller may control the operation of braking mechanism 50 and extension mechanism 56, and thus the resistance applied to pedal assembly 46 and tilt of frame structure 48, in response to various user inputs or other control signals. The exercise cycle controller can be incorporated within any part of exercise cycle 12b including frame structure 48 or control console 26b. An exercise cycle controller can also be incorporated within personal computers 18.

The moveable members on elliptical machine 12 include a pedal assembly 62. An actuator, such as a braking mechanism, may selectively adjust the rotational resistance applied to pedal assembly 62. The braking mechanism can comprise a friction brake, a magnetic brake, or any other suitable brake for controlling the rotational resistance applied to pedal assembly 62. Each of the actuators in elliptical machine 12c, including the braking mechanism, may be electrically connected to an elliptical machine controller. The elliptical machine controller may control the operation of the braking mechanism and thus the resistance applied to pedal assembly 62 in response to various user inputs or other control signals. The elliptical machine controller can be incorporated within any part of elliptical machine 12c including control console 26c. An elliptical machine controller can also be incorporated or within personal computers 18.

Referring again back to FIG. 1, a communication connection between exercise devices 12 and communication system 14 can be made in a variety of ways. For example, as depicted in FIG. 1, treadmill 12a may be capable of wireless communication directly with communication system 14 or through network 16. A "network" may comprise one or more data links that enable the transport of electronic data between computer systems and/or modules and/or other electronic devices. Thus, network 16 may be a communication network that enables various hardware and software modules and devices to communicate one with another. Specifically, network 16, may be a local area network (LAN), wide area network (WAN), wireless network, packetized network, real-time network, and the like. Network 16 may facilitate communication between communication system 14 and exercise devices 12.

Various types of ports or interfaces may be included within exercise devices 12 to enable wireless communication. For instance, an exercise device 12 may include one or more ports and interfaces to enable wireless communication through broadcast technology, including television broadcast over the airwaves, cable or cable modems, satellite, telephone lines, whether analog or digitally based, the Internet, DSL, G-Lite, wireless technology, infrared (IR) technology, other high-speed data connections, or any other suitable transmission technology or medium. The wireless communication between treadmill 12a and communication system 14 may be bidirectional.

In addition, communication with communication system 14 may be through a wired connection. In the illustrated embodiment, exercise cycle 12b is shown with a hardwire connection to personal computer 18, which itself has a hardwire connection with network 16. Alternatively, exercise cycle 12b may include a hardwire connection directly to network 16. The wired communication between exercise cycle 12b and communication system 14 may be bidirectional.

Further, communication with communication system 14 may be through a removable data storage device. In the illustrated embodiment, elliptical machine 12c includes a memory card port 23 that is configured to accept and read memory card 22. Memory card 22 may be in the form of any type of portable memory device. Examples of such devices include, but are not limited to, flash memory cards and USB-enabled memory devices. For instance, by way of example and not limitation, memory card 22 may be a Secure Digital (SD) card, a MultiMedia flash memory card (MMC), DataFlash device, CompactFlash device, removable NAND-type flash memory (e.g. SmartMedia, Sony Memory Stick), one-time-programmable memory cards (OTP), XD cards, and the like. Memory card 22 may receive data through personal computers 18 and/or directly from communication system 14. Memory card 22 may then deliver this information to elliptical machine 12c through memory card port 23.

In addition, memory card 12c may be used to transmit data from elliptical machine 12c to communication system 14. For example, elliptical machine 12c may upload data to memory card 22, which may then be uploaded to communication system 14 either directly or through personal computers 18.

As stated previously, communication system 14 may communicate with and gather data from one or more third parties 24 in order to create an exercise program. Generally, examples of a third party 24 may include: (i) a live human being; or (ii) a database, such as a website, computer, optical media (e.g., compact disk or digital video disk), visual media, or magnetic media (e.g., videotape, readable disk), an electronic monitoring system, dynamic computer readable instructions, interactive and/or dynamic software programs, computer readable instructions, one or more other databases, other media, hardware, and/or software modules and components. In some embodiments, a third party 24 may include MAPQUEST.COM, MAP.GOOGLE.COM, the GOOGLE EARTH database, the GTOPO 30 database, the GOOGLE STREET VIEW database, the MICROSOFT VIRTUAL EARTH database, the WIKIPEDIA database, EMUSIC.COM, AMAZON.COM, the ITUNES database, the PANDORA database, and the like. These are merely a few examples of third parties 24 that can be accessed to retrieve information and data that can be used to generate the above described exercise programming. It is understood that the exemplary third parties 24 noted herein are not an exclusive or exhaustive list of available third parties 24. Rather, the identified third parties 24 are provided simply by way of example.

One or more of these third parties 24 may store terrain data from one or more real world locations. The phrase "terrain data" as used herein may include altitude, slope, inclination levels, and/or other features of the terrain that may be simulated on an exercise device. In order to be simulated on an exercise device, the terrain data may be formatted, manipulated or converted into one or more control signals. The phrase "control signals" as used herein may include an instruction readable by an exercise device that may be implemented by exercise devices 12 to selectively adjust an operating parameter. For example, one or more control signals may selectively adjust the inclination level and/or tilt of tread base 36 on treadmill 12a, the resistance applied pedal assembly 46 and/or tilt of frame 48 on exercise cycle 12b, and/or the resistance applied pedal assembly 62 on elliptical machine 12c. Control signals may further include time, distance, and the like of an exercise program performed on exercise devices 12.

One or more of third parties 24 may store image data from one or more real world locations. The phrase "image data" may include one or more static images and/or one or more moving (i.e., video) images. For example, image data as used herein may include a plurality of sequential static images, a video display, and/or a single image of terrain to be traversed by a user, such as a mountain, race course, or street. The phrase "display signals," as used herein, includes image data that (if necessary) has been formatted, manipulated, or converted so that it can be displayed on the screen of an exercise device, such as display screens 28. Examples of such display signals include, for example, video programming, sequential static image programming, and/or a single image of terrain to be traversed.

One or more of these databases may further store audio data. The phrase "audio data" may include any audio material, including natural sounds associated with one or more real world locations, dialog, narration, sound effects, and/or music. The phrase "audio signals," as used herein, includes audio data that (if necessary) has been formatted, manipulated, or converted so that it can be presented through one or more audio output devices, such as output devices 30.

Terrain data, image data, and audio data may be stored not only by a third party 24, but may also be stored by personal computers 18, exercise devices 12, and/or communication system 14. Regardless of the source of the data, personal computers 18, exercise devices 12, and/or communication system 14 may use the terrain data, image data, and audio data to create an exercise program. Personal computers 18, exercise devices 12 and/or communication system 14 may format, manipulate, or convert the terrain data, image data, and audio data into control signals, display signals, and/or audio signals for an exercise program.

With access to at least some of the data described above, personal computers 18, exercise devices 12, and/or communication system 14 is able to generate exercise programming that allows exercise devices 12 to simulate real world environments. Specifically, the exercise program may include one or more control signals, display signals, and audio signals that together may simulate a real world exercise session. These signals may be synchronized. For example, control signals may be synchronized with display signals and/or audio signals so that the implementation of a control signal coincides with the display of a display signal and/or presentation of an audio signal. Display signals may be synchronized with control signals and/or audio signals so that the display of a display signal coincides with the implementation of a control signal and/or presentation of an audio signal. Audio signals may be synchronized with control signals and/or display signals so that the presentation of an audio signal coincides with the implementation of a specific control signal and/or display of a specific display signal.

Figure 8:
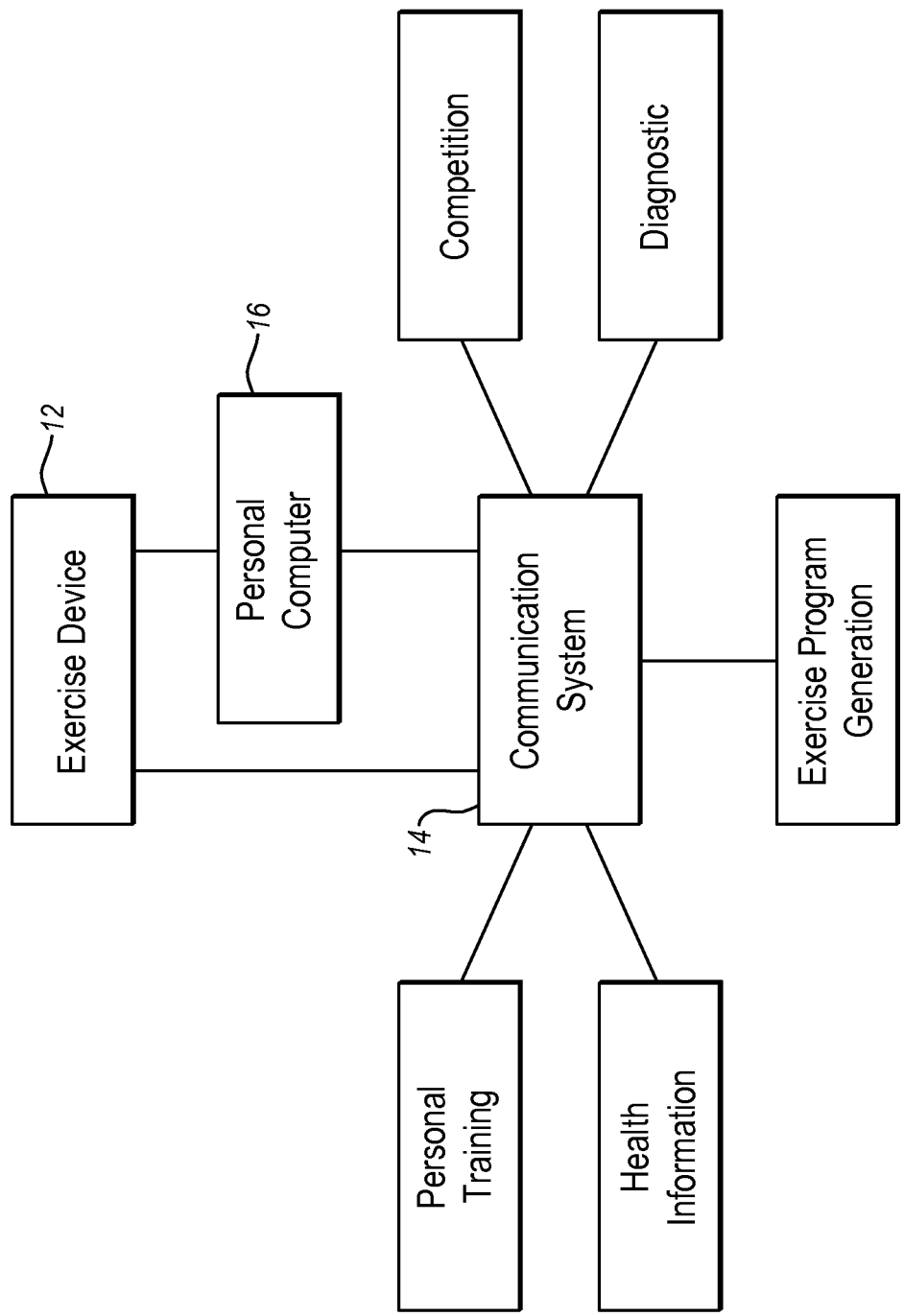
FIG. 8 is a functional block diagram of the process of connecting to a remote communication system and selecting one or more options available from the remote communication system.

Exercise devices 12, personal computers 18, and/or communication system 14 may provide a user with access to various different features. For example, as shown in FIG. 8, communication system 14 may provide a personal training option 64, health information, competition simulation feature, diagnostics, and exercise program generation. In addition to communication system 14, these features may be stored on memory card 22, within memory on exercise devices 12, and/or personal computers 18. Thus, while this discussion focuses on downloading or accessing the exercise programs and features directly or indirectly from communication system 14, these programs and features may also be available without requiring access to communication system 14 and/or network 16. Rather, these programs and features may be available from a built-in memory device on exercise devices 12, a removable memory device, such as memory card 22, or personal computers 18.

Figure 9:
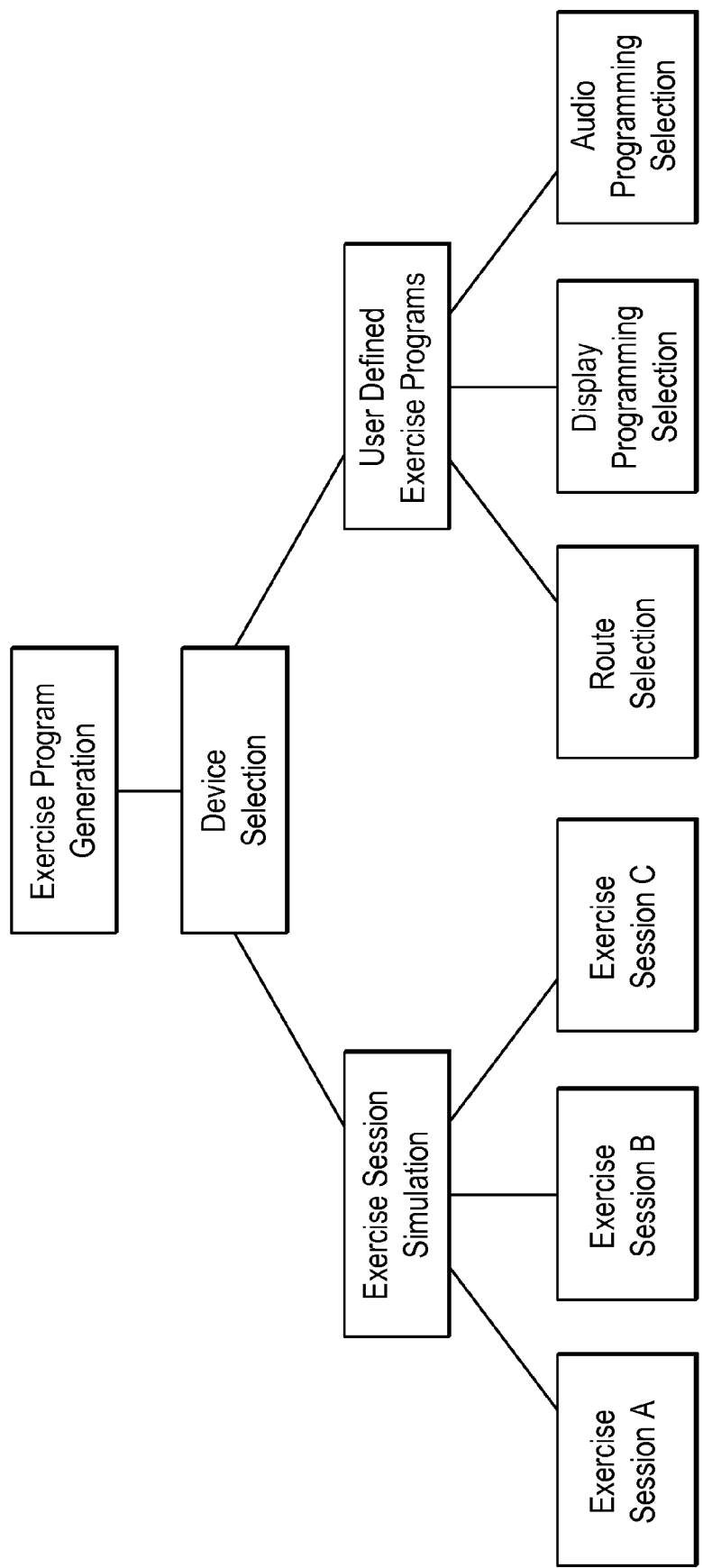
FIG. 9 is a flow diagram representing the process for selecting an exercise program in accordance with the teachings of the present invention.
Figure 10:
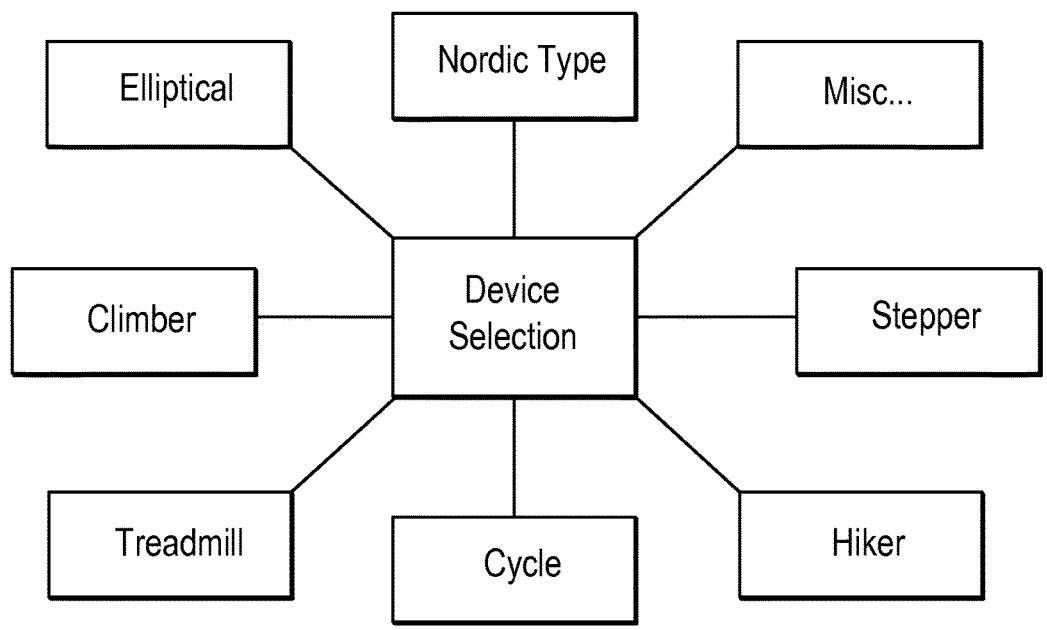
FIG. 10 is a functional block diagram of the process for selecting an exercise device to be used in connection with the exercise programs.

When a user selects the Exercise Program Generation option, a user may be able to access, select, create, and/or download exercise programming for use with an exercise device. As illustrated in FIG. 9, for example, after selecting the Exercise Program Generation option, communication system 14 may first prompt to the user to select the type of exercise device with which the exercise program will be used. FIG. 10 illustrates a functional block diagram of the process of selecting an exercise device to be used in connection with the exercise program. As seen in FIG. 10, the user may be given the option to select from among many different types of exercise devices, including treadmills, cycles, Nordic type skiers, climbers, hikers, steppers, ellipticals, and the like.

Regardless of whether a real world exercise session to be simulated was performed on foot (jogging or walking for example), on a bicycle, or another device, communication system 14 may create an exercise program that is compatible with all types of exercise devices. After selecting the type of exercise device to be used, the user can then select the desired exercise program that is compatible with the selected exercise device.

Referring back to FIG. 9, once a user identifies the type of exercise device upon which the exercise program will be used, the user may then be prompted to select the type of exercise program desired. For example, the user may choose between a User Defined Exercise Program option and an Exercise Session Simulation option. When a user selects a the User Defined Program option, communication system 14 may allow a user at exercise devices 12 or personal computers 18 to create or select various aspects of exercise programming that are suitable to the desires of the user. When creating a user defined exercise program, the user may have the option to select, among other things, a desired route, images to be displayed, and/or audio to be presented. The user may also have the option to select other exercise programming parameters, such as the exercise time, changes in the speed of one or more operating parameters, total calories to be burned, total distance to be traveled, total elevation change, themes for the programming, and the like.

By way of example, after selecting the User Defined Program option, the user may be able to select a real world environment which he or she would like simulated by an exercise program. In selecting the real world environment, the user may select a starting point, and ending point, and a specific route between the two. Alternatively, the user may select a starting point and an ending point, and allow communication system 14 and/or one or more of third parties 24 to select the route therebetween. In still other embodiments, the user may select a starting point and allow communication system 14 and/or one or more of third parties 24 to select a route that proceeds from the starting point for a selected time, distance, or the like. In yet other embodiments, the user may select a predefined route based on one or more characteristics of the route. Such characteristics may include distance, elevation change, historical significance, geographic characteristics, wild life, or plant life. A user may also select the type of audio programming to be presented.

When a user selects the Exercise Session Simulation option, the user can view and select from among one or more available exercise programs. These exercise programs may include real world exercise sessions performed previously by the user or other individuals. For example, the Exercise Session Simulation option illustrated in FIG. 9 includes an Exercise Session A, Exercise Session B, and Exercise Session C, each of which may simulate real world exercise sessions previously performed by one or more individuals. For example, Exercise Sessions A, B, and C may include control signals, display signals, and audio signals that are adapted to simulate the real world exercise sessions experienced by the one or more individuals and may be based upon information provided to communication system 14 regarding the real world exercise sessions performed by the one or more individuals.

The control signals may be adapted to simulate the environment of the real world exercise session, such as a trail, route, course, path, or the like traversed by the one or more individuals during their exercise sessions. For example, the control signals can be adapted to selectively adjust one or more operating parameters to simulate the hills, level surfaces, and the like, encountered in these locations. The display signals can be adapted to present visual images representative of what the one or more individuals may have seen during their exercise sessions. For example, the display signals can include still or moving images of the road, buildings, bridges, landscape, etc. that are seen along the trail, route, course, path, or the like traversed by the one or more individuals during their exercise sessions. The display signals may be presented in either 2D or 3D. The audio signals can be adapted to present sounds that the one or more individuals may have heard during their exercise sessions. For example, the audio signals can include typical outdoor sounds heard on the trail, route, course, path, or the like, including cars, sirens, horns, nature sounds, and the like. In addition, the audio signals may include dialog, narration, sound effects, and/or music that that the one or more individuals may have listened to during their exercise sessions. Still further, the audio signals may include a song playlist selected by the one or more individuals that previously performed the exercise sessions.

The control signals, display signals, and audio signals can be synchronized with each other. Synchronizing the control signals and the display signals may allow a user to view the real world environment at the same time the user encounters operating parameters that simulate the viewed real world environment. For example, as a user walks or runs on treadmill 12a, the control signals may cause treadmill 12a to simulate the terrain (i.e., hills, etc.) that a person would encounter while traversing the chosen route. As the user of treadmill 12a experiences the terrain of the route, the user can also view images, whether still or moving, of the route and its surroundings, which the control signals are simulating. Audio signals may be synchronized with control and display signals so that a user that is simulating a real world workout session will hear the same sounds heard by the individual that actually performed the real world exercise session. For example, the initiation of a certain song or series of songs may be synchronized with a specific portion of an exercise session, such as a steep hill.

For example, Exercise Session A may be an exercise program that simulates a bike ride that Lance Armstrong performed on the Pacific Coast Highway. Information, including for example the starting point and ending point of the ride and the music that Lance Armstrong listened to during the ride may be uploaded to communication system 14. Communication system 14 may create an exercise program that simulates everything from the terrain that Lance Armstrong traversed, what he saw, and what he heard. This exercise program may be implemented on any type of exercise device, including treadmills, exercise cycles, and elliptical machines.

Figure 11:
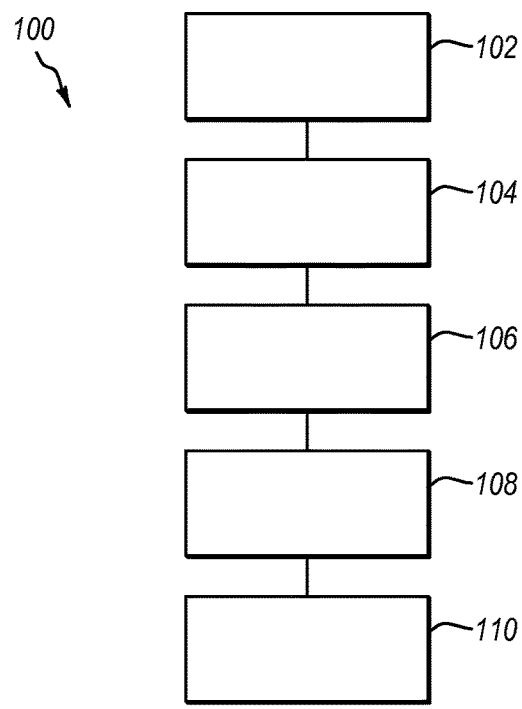
FIG. 11 illustrates a flow diagram showing steps that may be implemented in a method for generating an exercise program according to the present invention.

FIG. 11 is a functional block diagram that illustrates a process 100 that may be implemented to generate exercise programming via the Exercise Session Simulation option. In a first step 102, one or more individuals may access a communication system either directly or through a network. For example, an individual may use personal computers 18 to log onto communication system 14 via network 16.

Once the communication system is accessed by an individual, in a second step 102, he or she may input information regarding a real world exercise session that he or she previously performed. For example, an individual may use user input controls on a personal computer to upload information regarding a real world exercise session performed previously by that individual. In addition, details regarding an individual's real world exercise session may be uploaded using a portable device such as a GPS watch, telephone, or another portable device. Some information may be uploaded automatically, while other information may require some manual input. These details may include an identification of the route, trail, or path traveled, the distance traveled, the audio selection that the individual listened to during the real world exercise session, and the like.

Oftentimes, individuals do not listen to natural sounds during an exercise session. Some individuals, for example, may listen to music through a portable media player while walking, running, riding, or the like. Thus, details regarding the audio selection that the individual listened to during the real world exercise session may include a musical playlist of the songs that the individual listened to during the exercise session.

In a third step 106, the communication system may access additional data relating to the information regarding the real world exercise session. Specifically, terrain data, image data, and/or audio data may be accessed. This data may be used to generate the exercise program and may be stored at an exercise device, a personal computer, the communication system, and/or at one or more other locations, such as one or more third parties that are accessible via a network.

Terrain data relating to the route, trail, or path traveled by the individual may include map and topographical data relating to the route, trail, or path traveled by the individual. For example, the map and topographical data provided by one or more third parties may include a map highlighting the selected route, total route distance, route directions, travel times for specific speeds, as well as forward, backward, and side-to-side elevation changes along the selected route. Image data may include one or more static images and/or one or more moving (i.e., video) images of the route, trail, or path traveled by the individual. Audio data may include a digital formatted version of the audio selection listed to by the individual during the real world exercise session. For example, audio data provided by the one or more third parties may include .wav files, .mpeg-4 files, .mp3 files, or audio files in another audio file format.

In a fourth step 108, the communication system may convert, if necessary, and/or synchronize one or more of the terrain data, image data and audio data into control signals, display signals, and audio signals to create an exercise program. There are multiple route planning and mapping software applications and programs which can be accessed by the communication system to develop a route for exercise programming as described herein. Examples of such are MAPQUEST.COM, MAPS.GOOGLE.COM, GOOGLE EARTH (available at earth.google.com), and the like. Similarly, there are multiple databases that store topographical data for specific regions of the world. For example, the U.S. Geological Survey maintains a database, the GTOPO 30 or Global Topography at 30 arc/second database (available at edc.usgs.gov) includes topographical data for the entire world.

The communication system may use the map and topographical data to generate a series of control signals that control one or more operating parameters of an exercise device. In other words, using a correlation algorithm, the communication system can synchronize the topographical data with the map data to correlate the distance and the grade or elevation change between a starting and ending point and generate a control signal that will cause an exercise device to simulate that terrain. For instance, the communication system can use the map data to determine that the distance between point A and point B is ½ mile, and can use the topographical data to determine that the area between points A and B has a grade of 12%. Using this information, the communication system can generate one or more control signals that will cause a treadmill, for example, to incline its tread base to a 12% grade until the user has walked for ½ mile. In a similar manner, the communication system can use the map data, the topographical data, and other reference points along the selected route to generate control signals that control the side to side tilt of the tread base.

In addition to generating the control signals, the communication system can also generate display signals to accompany the control signals. As mentioned above, the display signals can include still or moving images of the selected real world route, which the communication system can retrieve from one or more third parties. For example, the Google Street View database may be accessed via the Google Maps API (application programming interface) to retrieve a series of images from of the selected real world route. When a series of images are used to provide a visual depiction of the selected rout, the images can be cached or buffered so that upon delivery to the user of an exercise device, the images provide an almost seamless, video-like depiction of the selected real world route.

As mentioned above, the display signals can be synchronized with the control signals. In this manner, the control signals will adjust the operating parameters of an exercise device at the same time the display signals depict a change in the terrain of the real world route. For instance, at the same time the control signals begin to cause a treadmill's tread base to incline to simulate a hill on the real world route, the display signals shows one or more images of the hill on the real world route as if the user were actually beginning to ascend the hill.

Once the control signals have been generated from the topographical/map data and the display programming from the retrieved images of the real world route, a correlation algorithm can be employed to synchronize the control signals with the display signals. In one embodiment, the correlation algorithm uses data about the series of retrieved images, such as the number of images along the real world route, the real world distances between the images, and the like. Similarly, the correlation algorithm also uses information from the retrieved topographical/map data, such as distances between locations on the real world route, changes in elevation between locations on the real world route, directional changes along the real world route, and the like. Using this data, the correlation algorithm synchronizes the control signals and the display signals. For example, the correlation algorithm may coordinate the first control signal with the display of the first image of the remote real world route. The correlation algorithm may correlate a subsequent image with a change in the map data, such as when the map data indicates a change in a certain distance from the previous real world location. The correlation algorithm may also correlate subsequent images with a change in the topographical data, such as an elevation change from the previous real world location.

As noted above, the exercise program can also include audio signals that may or may not be synchronized with the control signals and the display signals. The audio programming can include sounds that may typically be heard along the real world route, such as cars, sirens, animals, people, and the like. The audio signals can also include music that the individual listened to during the real world exercise session.

Once created, the communication system may make the exercise program available for download by one or more exercise devices in a fifth step 110. For example, a user of an exercise device may access the Exercise Session Simulation module via input devices on a control console. The Exercise Session Simulation module, which may be resident on a communication system, provides a user interface that allows the user to select the Exercise Simulation Option, as shown in FIG. 9.

Once the exercise programming has been delivered to an exercise device via any suitable means, such as those described herein, the exercise device can run/execute the exercise program simulating the real world exercise session by processing the control signals, the display signals, and/or the audio signals. As the exercise device executes the exercise program, terrain characteristics of the route, trail, or path traveled by the individual may be simulated. In particular, the control signals of the exercise programming may cause the exercise device to adjust one or more operating parameters, such as the incline or tilt of a tread base, to replicate the terrain of the route, trail, or path. In addition, display signals and audio signals may replicate what the individual saw and heard during the real world exercise session.

As noted above, an exercise device can monitor its actual operating parameters, such as the incline and tilt of a tread base and the speed of belt on a treadmill. The actual operating parameters of the exercise device and the exercise program can be correlated so that the control signals, display signals, and possibly audio signals are updated or changed at the appropriate times. For instance, the exercise program may include control signals that incline a tread base to a 5% grade for ¼ mile and then decline tread base to a 2% grade for 1 mile. The speed of a belt will affect the amount of time that each of the controls signals is active. If the belt were moving at 5 miles per hour (mph), for example, the user would traverse the ¼ mile segment in 3 minute and the 1 mile segment in 12 minutes. If the belt were moving at 2.5 mph, however, it would take the user 6 minutes to traverse the ¼ mile segment and 24 minutes to traverse the 1 mile segment. Thus, correlating or synchronizing the actual operating parameters of an exercise device with the exercise program allows the exercise device to be controlled in such a way as to realistically simulate the real world environment. The correlation or synchronization of the exercise programming and the actual operating parameters can be performed by an exercise device controller, a personal computer, a communication system, or a combination thereof.

Embodiments of the present disclosure may comprise or utilize a special purpose or general-purpose computer including computer hardware, such as, for example, one or more processors and system memory, as discussed in greater detail below. Embodiments within the scope of the present disclosure also include physical and other computer-readable media for carrying or storing computer-executable instructions and/or data structures. Such computer-readable media can be any available media that can be accessed by a general purpose or special purpose computer system. Computer-readable media that store computer-executable instructions are computer storage media (devices). Computer-readable media that carry computer-executable instructions are transmission media. Thus, by way of example, and not limitation, embodiments can comprise at least two distinctly different kinds of computer-readable media: computer storage media (devices) and transmission media.

Computer storage media (devices) includes RAM, ROM, EEPROM, CD-ROM, solid state drives ("SSDs") (e.g., based on RAM), flash memory, phase-change memory ("PCM"), other types of memory, other optical disk storage, magnetic disk storage or other magnetic storage devices, or any other medium which can be used to store desired program code means in the form of computer-executable instructions or data structures and which can be accessed by a general purpose or special purpose computer.

When information is transferred or provided over a network or another communications connection (either hardwired, wireless, or a combination of hardwired or wireless) to a computer, the computer properly views the connection as a transmission medium. Transmissions media can include a network and/or data links which can be used to carry desired program code means in the form of computer-executable instructions or data structures and which can be accessed by a general purpose or special purpose computer. Combinations of the above should also be included within the scope of computer-readable media.

Further, upon reaching various computer system components, program code means in the form of computer-executable instructions or data structures can be transferred automatically from transmission media to computer storage media (devices) (or vice versa). For example, computer-executable instructions or data structures received over a network or data link can be buffered in RAM within a network interface module (e.g., a "NIC"), and then eventually transferred to computer system RAM and/or to less volatile computer storage media (devices) at a computer system. Thus, it should be understood that computer storage media (devices) can be included in computer system components that also (or even primarily) utilize transmission media.

Computer-executable instructions comprise, for example, instructions and data which, when executed at a processor, cause a general purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the present disclosure may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, tablets, pagers, routers, switches, and the like. The present disclosure may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

INDUSTRIAL APPLICABILITY

In general, embodiments of the present disclosure relate to exercise systems and methods that enable a user to simulate a real world exercise session previously performed by an individual. The system may include an exercise device with one or more selectively adjustable operating parameters. It should be understood that the invention is not limited to any particular type of exercise device. To the contrary, the term "exercise device" may include any type of exercise machine, including, but not limited to, treadmills, exercise cycles, Nordic style ski exercise devices, rowers, steppers, hikers, climbers, and elliptical or striding exercise devices.

For instance, a treadmill may have one or more adjustable incline mechanisms for allowing the treadmill to simulate a descent down a hill, an ascent up a hill, or traversing across a hill. The exercise device may also include one or more display screens that may display images from real world locations. The exercise device may further include an audio out port for presenting an audio selection. For example, the exercise device may include a speaker or a port to which headphones, for example, may be connected.

The system may further include a communication system into which an individual may input information regarding a previous real world exercise session. Any individual may input information regarding a previous real world exercise session. In one embodiment of the present invention, famous individuals such as celebrities may input information regarding a real world exercise session.

Information regarding a real world exercise session may be uploaded to the communication system directly or through any device that is able to communicate with the communication system. For example, an individual may upload information to the communication system via a personal computer, mobile device such as a telephone, an exercise device, and the like. The uploaded information may include an identification of the road, trail, or path traveled and the distance traveled. The uploaded information may also include an identification of the audio selection listened to by the individual during the exercise session. The uploaded information may also include other details regarding the exercise session such as but not limited to weather conditions, the time during the day or night when the exercise session occurred, whether the individual was on foot or rode a bike, and the like.

The communication system may use the information uploaded by the individual to create an exercise program that simulates the real world exercise session performed by the individual. For example, the communication system may use the identification of the road, trail, or path traveled to create control signals that cause the exercise device to simulate the terrain traversed by an individual during a real world exercise session in an automatic and/or dynamic manner. For example, the control signals may simulate the hills and flat areas that the individual traveled during the real world exercise session. The communication system may also use the identification of the road, trail, or path traveled to create display signals that cause images from the road, trail, or path traveled to be shown on a display screen. The communication system may further use the identification of the audio selection listened to by the individual during the exercise session to create audio signals that duplicate the audio selection that the individual listened to during the exercise session.

The communication system may access additional data to transform the information uploaded by the individual into an exercise program that includes control signals, display signals, and audio signals. For example, the communication system may access one or more map or topographical databases to construct control signals that realistically simulate the terrain traversed by the individual. The communication system may also access these databases or others to create display signals that include actual images from the road, trail, or path traveled by the individual. The communication system may further access one or more audio databases to construct audio signals from the information provided by the individual regarding the sounds that he or she heard during the exercise session. The additional data accessed by the communication system may reside within the communication system itself. Alternatively, the communication system may access the additional data from one or more third parties.

Once an exercise program is created, it may be made available to users of exercise devices. In order to acquire the exercise program, the exercise device may communicate with the communication system. As described herein, there are many different ways that an exercise device may communication with a communication system. For example, an exercise device may communicate directly with the communication system via a wired or wireless connection. Alternatively, an exercise device may communicate with the communication system indirectly via a network. Alternatively still, an exercise device may communicate with the communication system via a data storage device such as a memory card. With regard to the memory card embodiment, a user may access the communication system via a personal computer. The user may download a desired exercise program to the memory card, which may be inserted into a port in the personal computer. Once the desired exercise program has be uploaded to the memory card, the memory card may be inserted into an appropriately sized port on an exercise device. The exercise device may then upload the exercise program to memory within the exercise device or run the program directly from the memory card.

The communication system may include an interface for assisting a user in choosing a desired exercise program. For example, the communication system may present a user with a list of names of individuals whose real world exercise sessions may be simulated. Alternatively, the communication system may categorize the exercise sessions based on level of difficulty, distance, location, audio selection or another parameter. The user may then be presented with options based on these parameters and directed to the appropriate category of exercise programs.

The invention claimed is:

1. In an exercise system having a remote communication system adapted to communicate with a plurality of exercise devices, a method for generating an exercise program comprising:
    receiving at a remote communication system route information identifying a route traveled by an individual during a real world exercise session, the remote communication system comprising one or more processors for processing the route information;
    generating an exercise program from the route information, the exercise program comprising control signals that cause a first exercise device and a second exercise device to substantially simulate topographical characteristics of the route traveled by the individual during the real world exercise session;
    sending the exercise program to the first exercise device, the first exercise device including one or more first movable members;
    receiving the exercise program at the first exercise device;
    programming the first exercise device to perform the exercise program, the control signals of the exercise program selectively adjusting the one or more first movable members of the first exercise device to simulate the real world exercise session;
    sending the same exercise program that was sent to the first exercise device to the second exercise device, the second exercise device including one or more second movable members, the first exercise device and the second exercise device being different types of exercise devices;
    receiving the exercise program at the second exercise device; and
    programming the second exercise device to perform the exercise program, the control signals of the exercise program selectively adjusting the one or more second movable members of the second exercise device to simulate the real world exercise session.

2. The method of claim 1, wherein the route information is received from a device that senses the route information during the real world exercise session and communicatively transfers the route information to the remote communication system.

3. The method of claim 1 further comprising retrieving data from a third party regarding the route traveled by the individual during the real world exercise session.

4. The method of claim 1 further comprising retrieving data from a third party regarding a musical selection listened to by the individual during the real world exercise session.

5. The method of claim 1, wherein the exercise program further comprises display signals that cause the first exercise device to display images of the route traveled by the individual during the real world exercise session.

6. The method of claim 5 further comprising retrieving data from a third party regarding the route traveled by the individual during the real world exercise session, wherein the third party data is used to generate the display signals.

7. The method of claim 5, wherein the display signals comprise video images.

8. The method of claim 5 further comprising synchronizing the control signals and the display signals.

9. The method of claim 1, wherein the first exercise device is a treadmill and the control signals of the exercise program cause an actuator associated with a treadmill tread base to adjust an inclination of the tread base.

10. The method of claim 9, wherein the control signals of the exercise program cause the actuator associated with the treadmill tread base to adjust a side to side tilt of the tread base.

11. The method of claim 1, wherein the first exercise device is an exercise cycle;
    wherein the one or more first movable members of the first exercise device comprise one or more pedals of the exercise cycle; and
    wherein the control signals of the exercise program cause an actuator associated with the one or more pedals of the first exercise device to adjust a rotational resistance applied to the pedals.

12. The method of claim 11, wherein the control signals of the exercise program cause an actuator associated with an exercise device frame to adjust a tilt of the exercise device frame.

13. The method of claim 1 further comprising making the exercise program available for download to the first exercise device and the second exercise device.

14. The method of claim 13, wherein the exercise program is available for download to the first exercise device and the second exercise device via the Internet.

15. The method of claim 1 further comprising receiving audio information identifying a musical selection listened to by the individual during the real world exercise session.

16. A system that generates an exercise program for two or more different types of exercise devices, the system capable of communicating the same exercise program that was sent to the first exercise device to a second exercise device and communicating the exercise program to a second exercise device, the system comprising:
    a first exercise device comprising a first movable element that moves during the performance of an exercise, the first movable element including a first operating parameter that is selectively adjustable;

a second exercise device comprising a second movable element that moves during the performance of an exercise, the second movable element including a second operating parameter that is selectively adjustable;

a remote communication system that can communicate with the first exercise device and the second exercise device, the remote communication system being receptive to receive data identifying a real world exercise route traveled by an individual during an exercise session, the remote communication system including one or more processors for processing the received data relating to the real world exercise route; and a single exercise program for both the first exercise device and the second exercise device based upon the received data, the first exercise device and the second exercise device being different types of exercise devices, the exercise program comprising control signals that selectively adjust the first operating parameter of the first movable element of the first exercise device to simulate terrain characteristics of the real world exercise route and display signals that include visual images of the real world exercise route, the exercise program being communicated to the first exercise device and the first exercise device being capable of performing the exercise program.

17. The system of claim 16 further comprising audio signals representative of the playlist of songs listened to by the individual during the exercise session.

18. The system of claim 16, wherein the remote communication system communicates with the first exercise device via a portable memory device.

19. The system of claim 16, wherein the control signals selectively adjust an inclination level of a treadmill tread base.

20. A computer system, comprising:
one or more processors;
system memory; and
one or more computer storage media having stored thereon computer-executable instructions which, when executed by the one or more processors, cause the computer system to implement a method for generating a single exercise program for both of two different types of exercise devices, the method for generating the exercise program comprising:

receiving route information identifying a route traveled by an individual during a real world exercise session;

using the route information to generate the single exercise program for both of two different types of exercise devices that simulate the real world exercise session on the different types of exercise devices, the exercise program comprising:

first control signals that cause a first type of exercise device to substantially simulate topographical characteristics of the route traveled by the individual during the real world exercise session, the first type of exercise device comprising a first movable element, the first control signals selectively adjusting the first movable element to simulate the real world exercise session; and second control signals that cause a second type of exercise device to substantially simulate topographical characteristics of the route traveled by the individual during the real world exercise session, the second type of exercise device comprising a second movable element, the second control signals selectively adjusting the second movable element to simulate the real world exercise session; and transferring the exercise program to a first exercise device of the first type of exercise devices; and programming the first exercise device of the first type of exercise devices to perform the exercise program.

21. The computer system of claim 20, wherein the method further comprises:
transferring the exercise program to a first exercise device of the second type of exercise devices; and
programming the first exercise device of the second type of exercise devices to perform the exercise program.

* * * * *